(12) United States Patent
Koyama

(10) Patent No.: US 12,396,904 B2
(45) Date of Patent: Aug. 26, 2025

(54) ABSORBENT ARTICLE

(71) Applicant: DAIO PAPER CORPORATION, Shikokuchuo (JP)

(72) Inventor: Hidetoshi Koyama, Tochigi (JP)

(73) Assignee: Daio Paper Corporation, Ehime (JP)

( * ) Notice: Subject to any disclaimer, the term of this patent is extended or adjusted under 35 U.S.C. 154(b) by 360 days.

(21) Appl. No.: 18/006,836

(22) PCT Filed: May 25, 2021

(86) PCT No.: PCT/JP2021/019765
§ 371 (c)(1),
(2) Date: Jan. 25, 2023

(87) PCT Pub. No.: WO2022/054347
PCT Pub. Date: Mar. 17, 2022

(65) Prior Publication Data
US 2023/0270604 A1    Aug. 31, 2023

(30) Foreign Application Priority Data

Sep. 10, 2020    (JP) .................................. 2020-152251

(51) Int. Cl.
*A61F 13/62*    (2006.01)
*A61F 13/15*    (2006.01)

(52) U.S. Cl.
CPC .. *A61F 13/622* (2013.01); *A61F 2013/15146* (2013.01)

(58) Field of Classification Search
CPC .. A61F 13/5605; A61F 13/5611; A61F 13/62; A61F 13/622; A61F 13/625;
(Continued)

(56) References Cited

U.S. PATENT DOCUMENTS

| 5,300,058 A | 4/1994 | Goulait |
| 5,953,797 A * | 9/1999 | Provost ................. B29C 43/222 24/304 |

(Continued)

FOREIGN PATENT DOCUMENTS

| JP | H08507227 A | 8/1996 |
| JP | 2001129011 A | 5/2001 |

(Continued)

OTHER PUBLICATIONS

International Search Report for PCT/JP2021/019765, dated Jul. 13, 2021.

(Continued)

*Primary Examiner* — Catharine L Anderson
(74) *Attorney, Agent, or Firm* — Andrus Intellectual Property Law, LLP

(57) ABSTRACT

An absorber with a top sheet, covering the other surface of the absorber with a back sheet, and attaching a hook member of a mechanical fastener to each of a front side and a back side of the back sheet. The hook member is formed of a sheet-like base portion and a large number of hook portions. Each of the hook portions has a support column extending from the base portion to a side opposite to the back sheet and a protruding portion which is located at an end of the support column and in which a length of a protrusion extending toward a distal end portion side of each of the front side and the back side is longer than a length of a protrusion extending toward a crotch portion.

5 Claims, 15 Drawing Sheets

(58) Field of Classification Search
CPC ............ A44B 18/0003; A44B 18/0015; A44B 18/0019; A44B 18/0038; A44B 18/0042; A44B 18/0061; A44B 18/0065
See application file for complete search history.

(56) References Cited

U.S. PATENT DOCUMENTS

| | | | |
|---|---|---|---|
| 9,717,309 B2* | 8/2017 | Marche | ............... A44B 18/0065 |
| 2006/0090307 A1 | 5/2006 | Mcdaniel | |
| 2009/0035539 A1* | 2/2009 | Selinfreund | ......... G11B 23/282 |
| | | | 428/201 |
| 2017/0156451 A1* | 6/2017 | Cheng | ................ A44B 18/0065 |
| 2020/0214911 A1 | 7/2020 | Nakaoka | |

FOREIGN PATENT DOCUMENTS

| | | | |
|---|---|---|---|
| JP | 2009189701 A | 8/2009 | |
| JP | 2013000286 A | 1/2013 | |
| JP | 2013212214 A | 10/2013 | |
| JP | 2014209992 A | 11/2014 | |
| JP | 2015096113 A | 5/2015 | |

OTHER PUBLICATIONS

Extended European Search Report for European Patent Application No. 21866308.6, dated May 16, 2024.

* cited by examiner

[FIG.1]
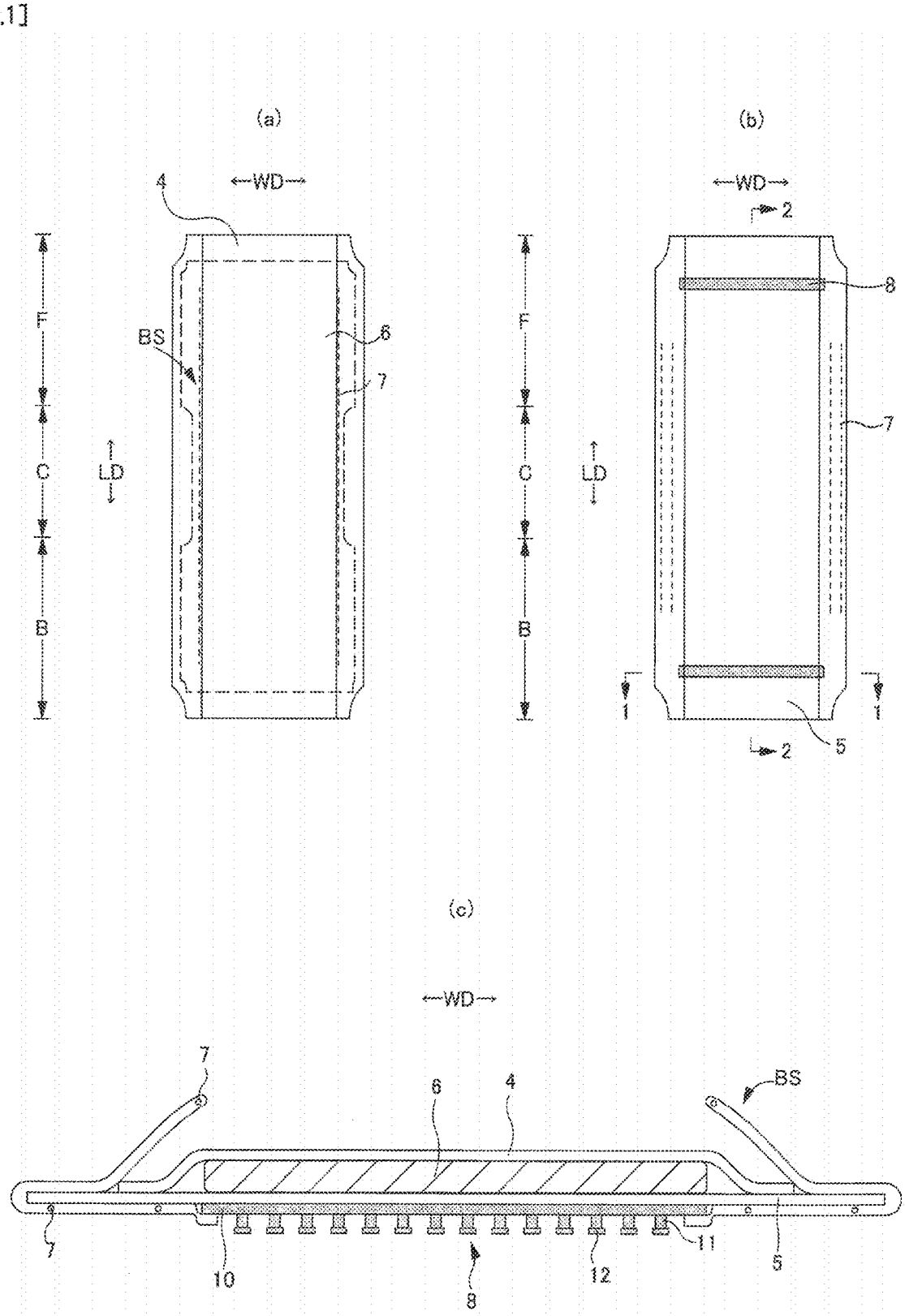

[FIG.2]
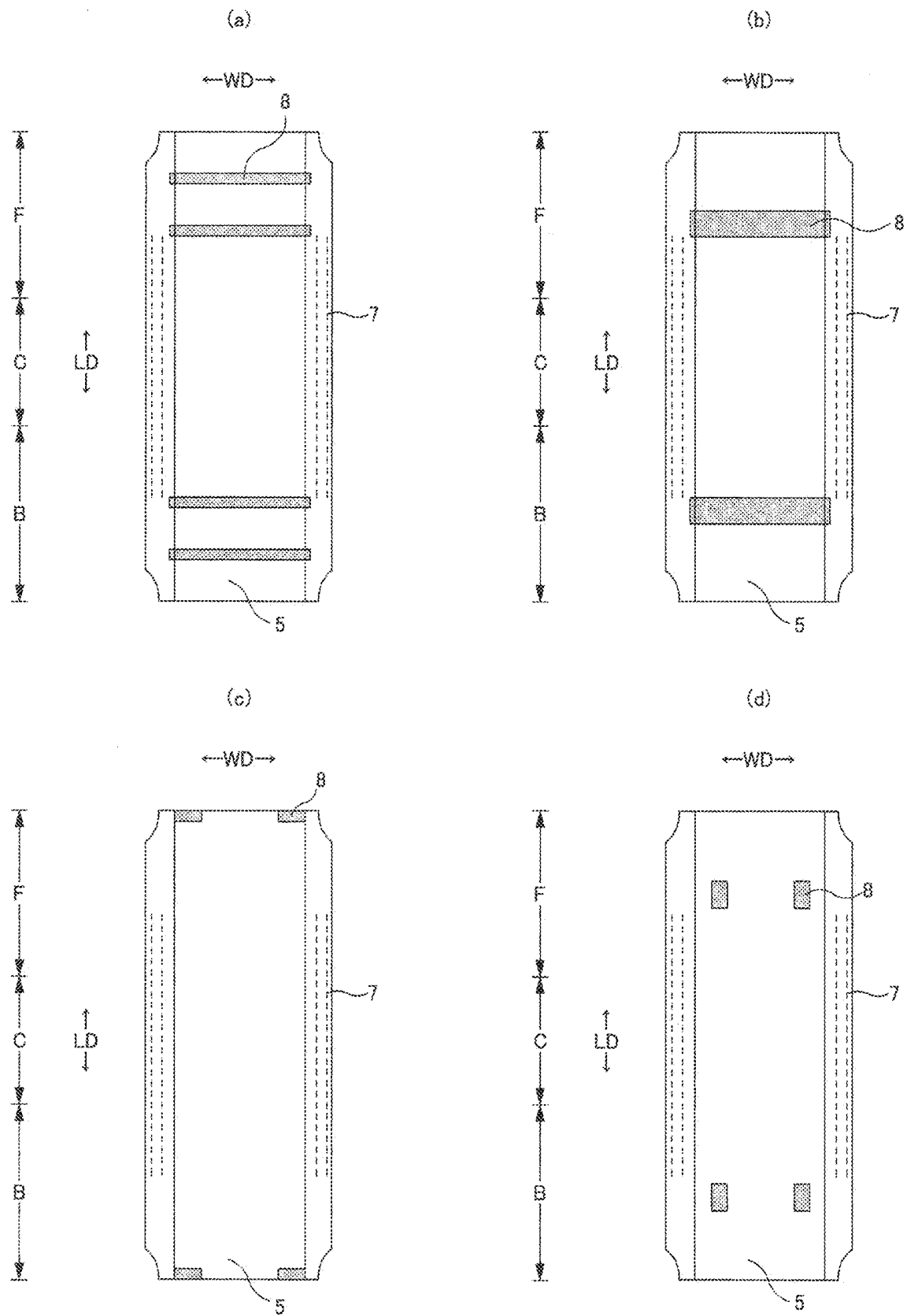

[FIG.3]
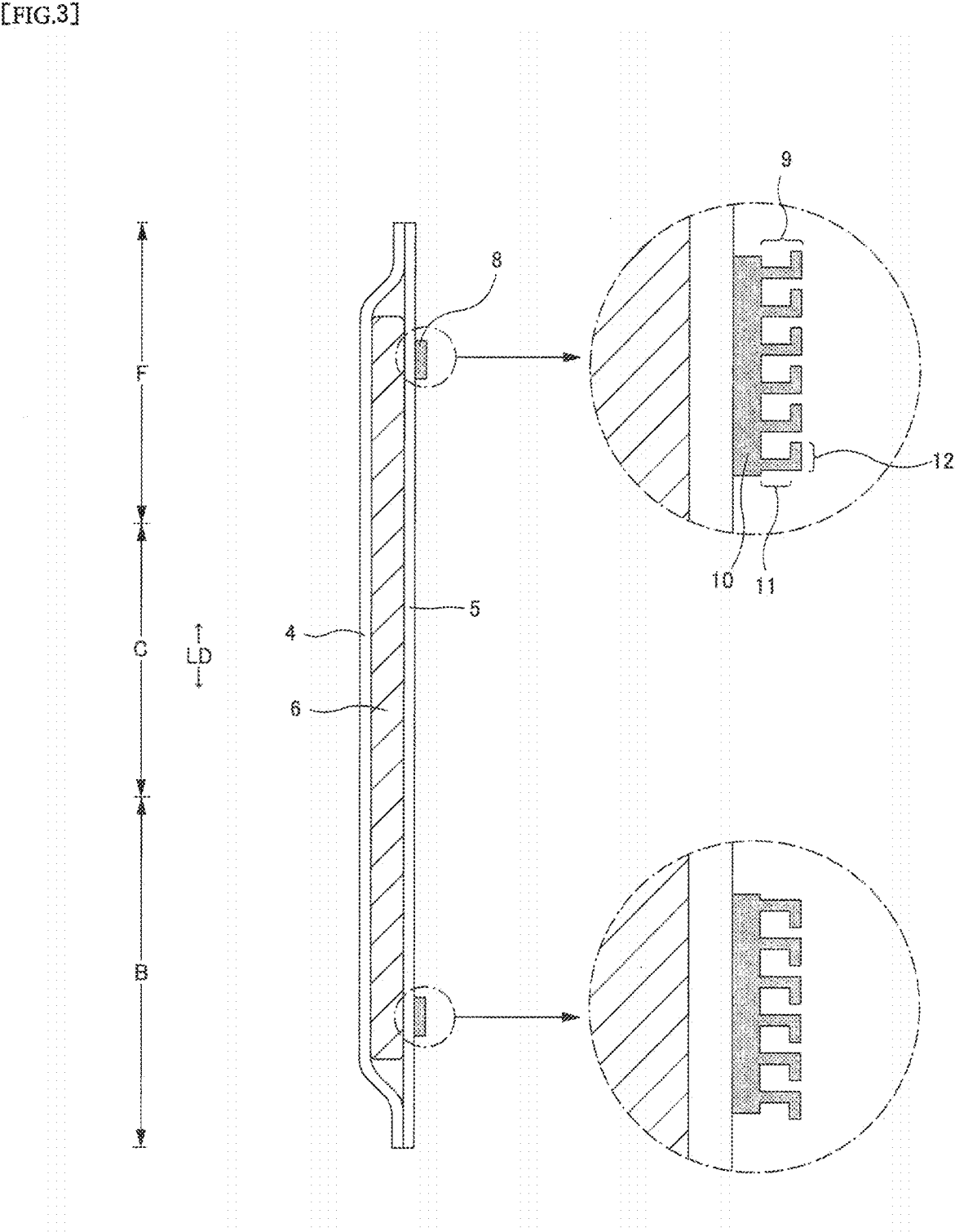

[FIG.4]
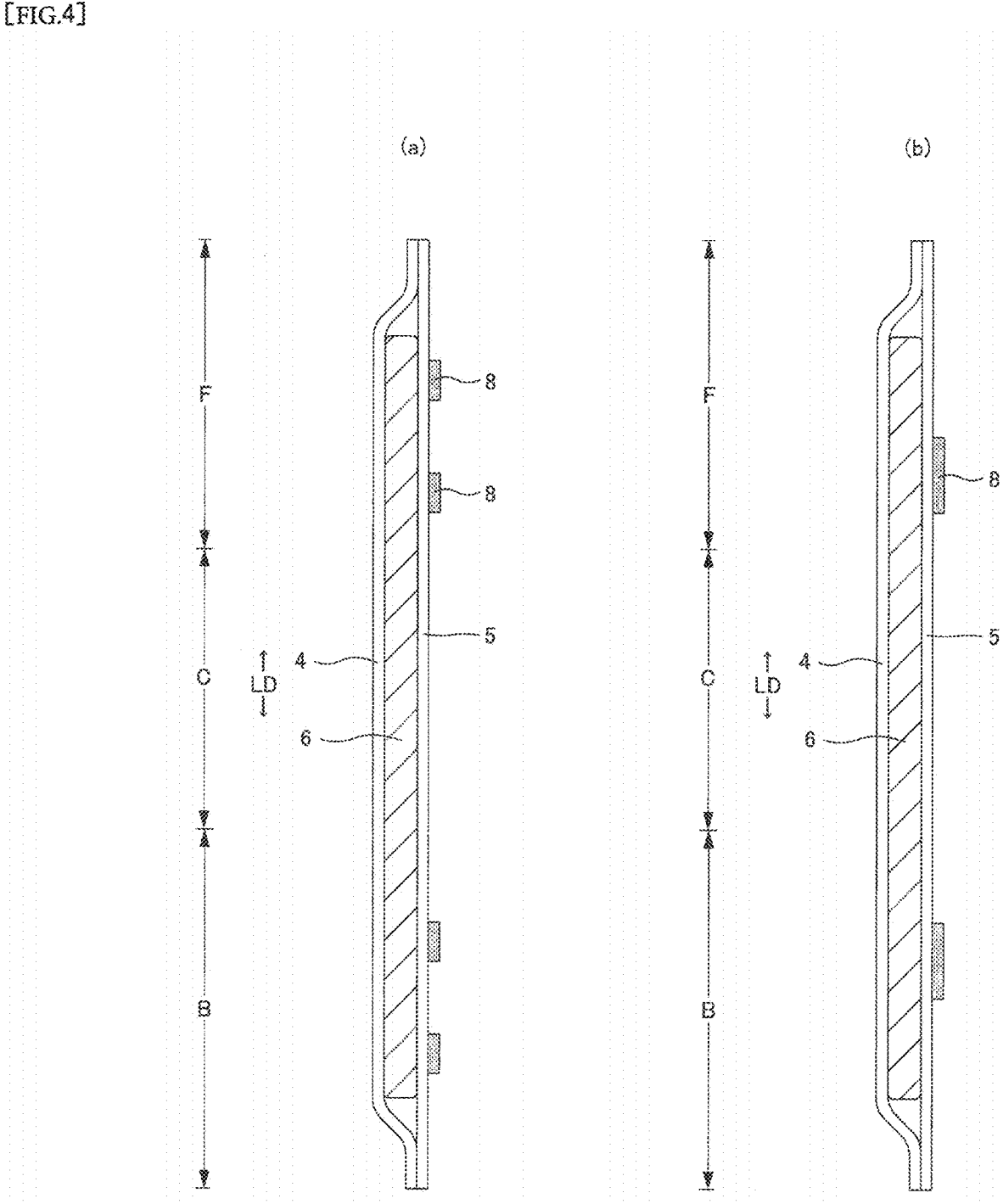

[FIG.5]
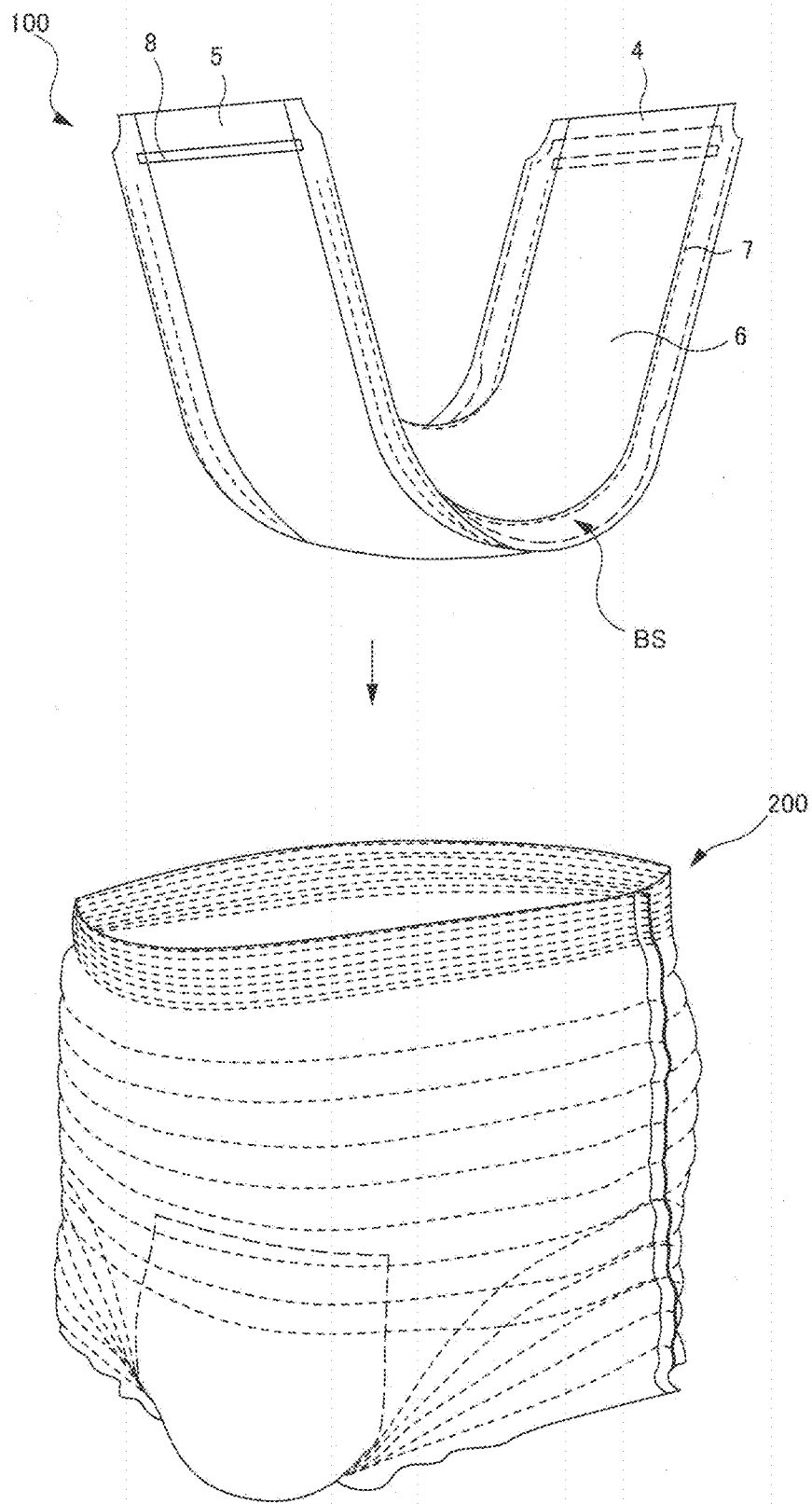

[FIG.6]
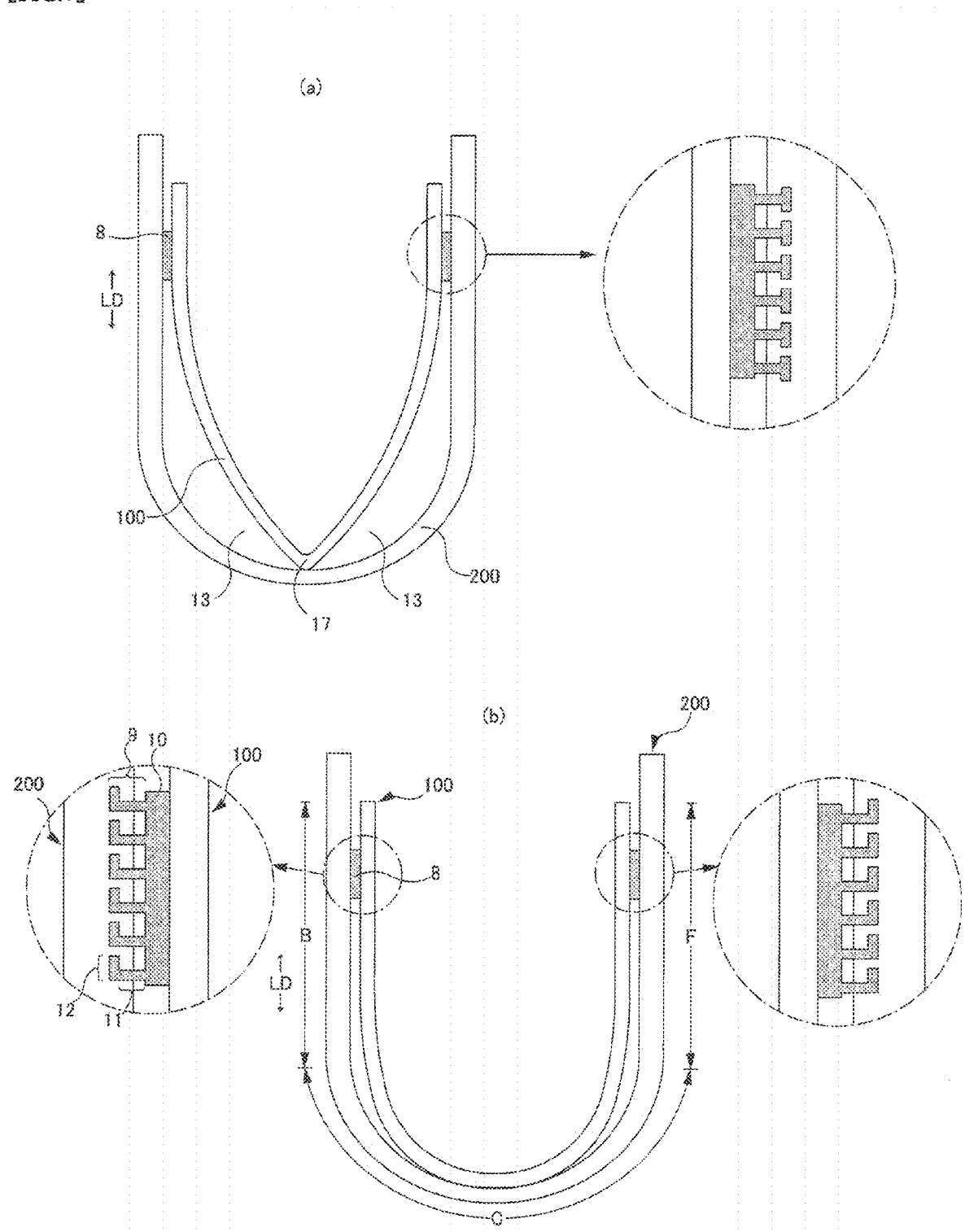

[FIG.7]
(a)
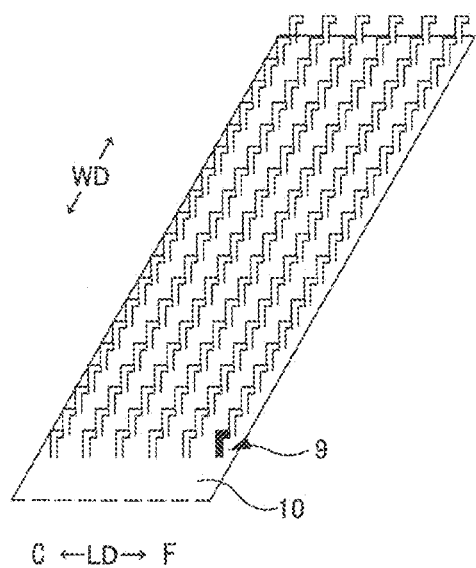
(b)
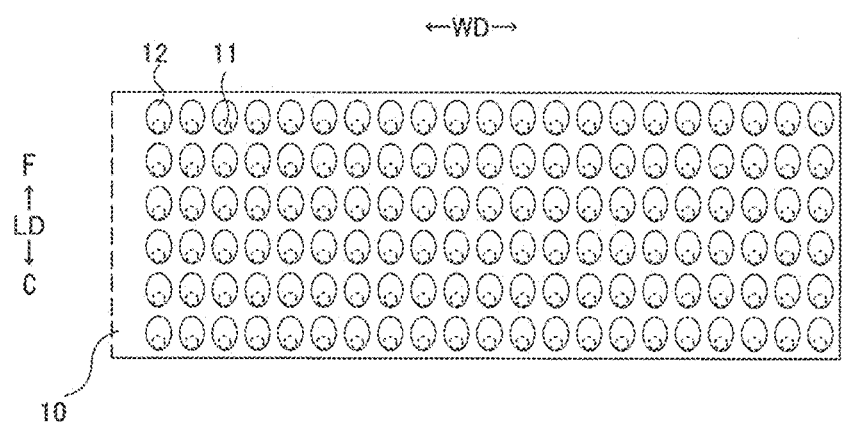

[FIG.8]
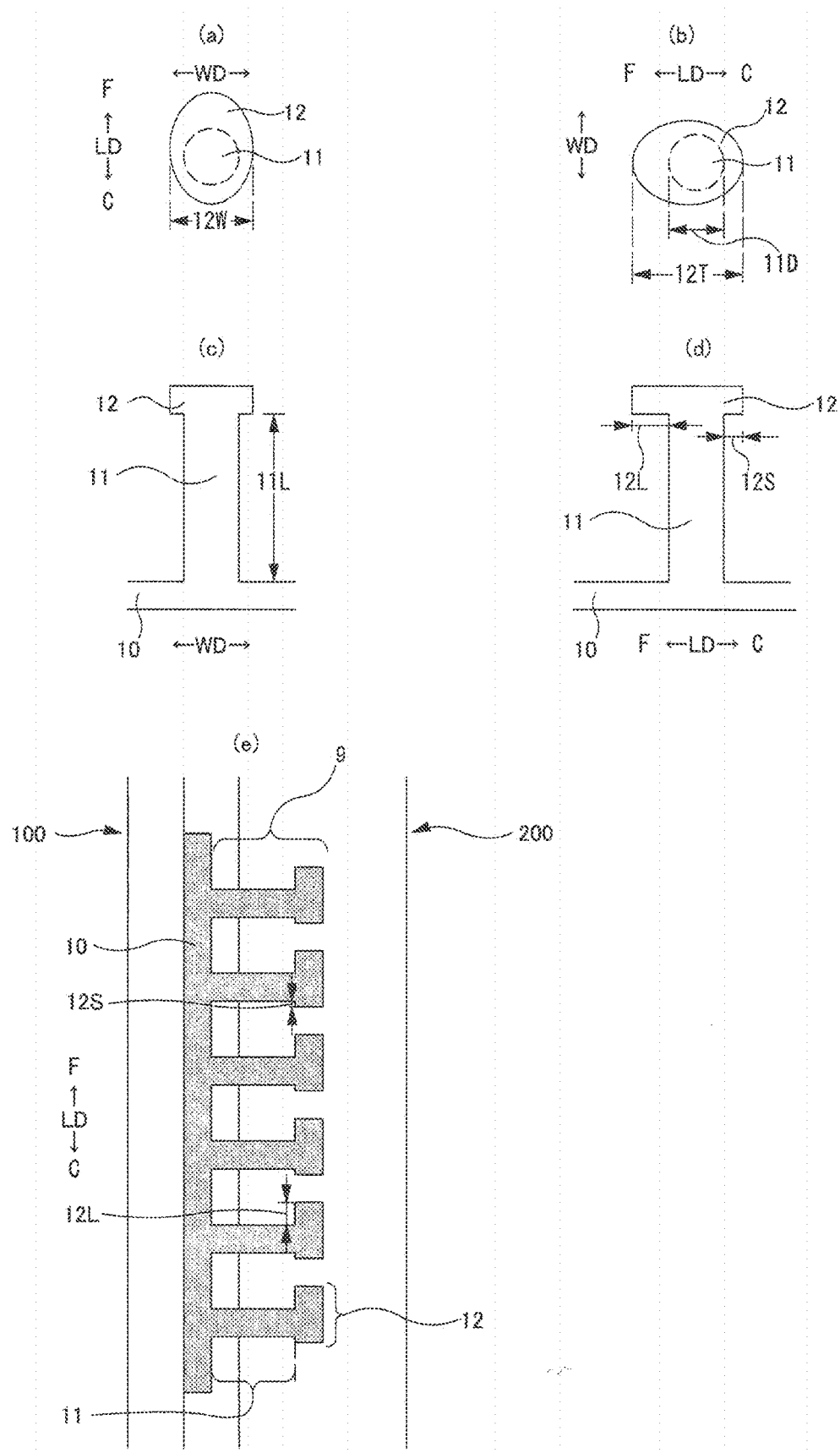

[FIG.9]
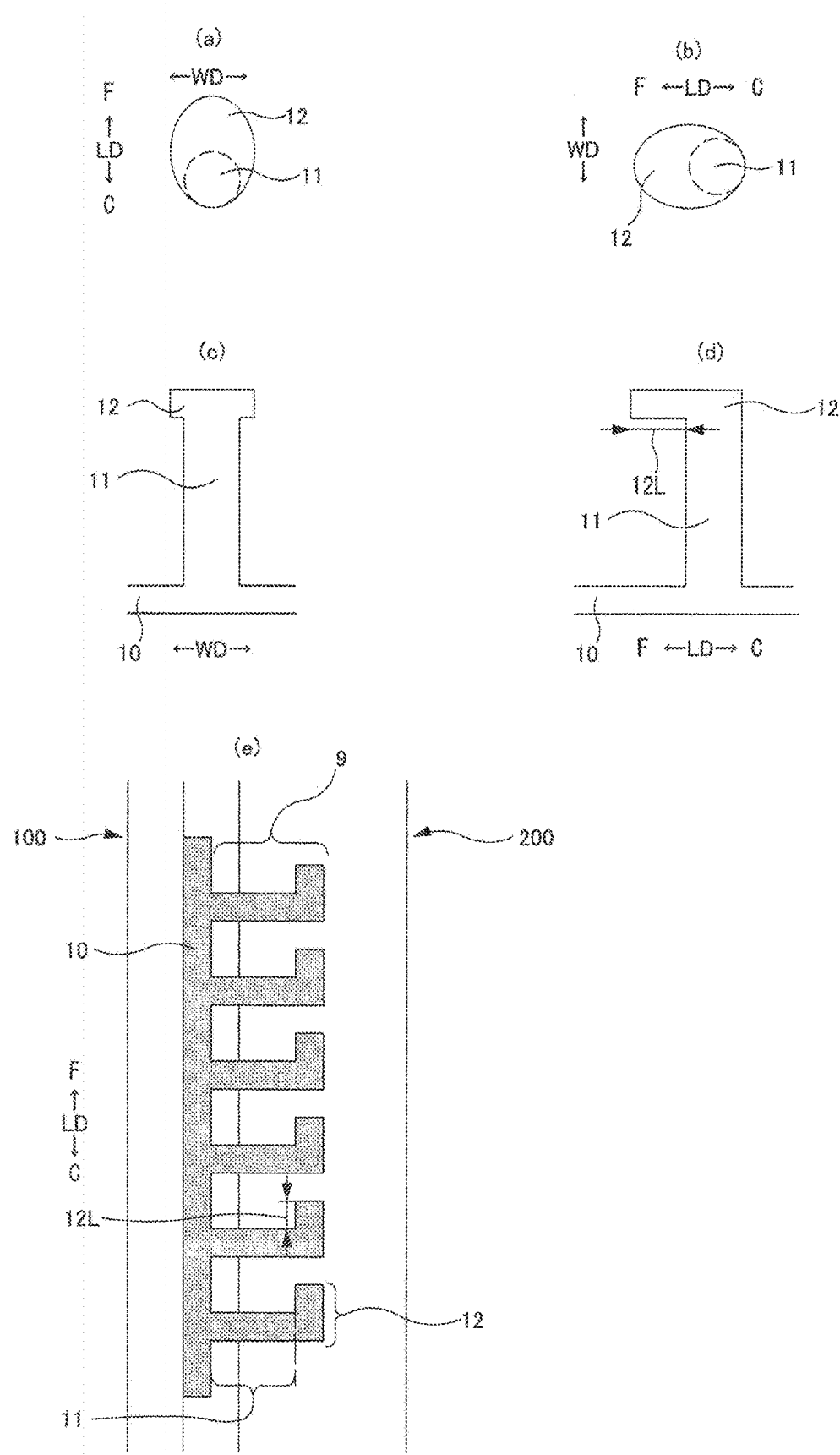

[FIG.10]
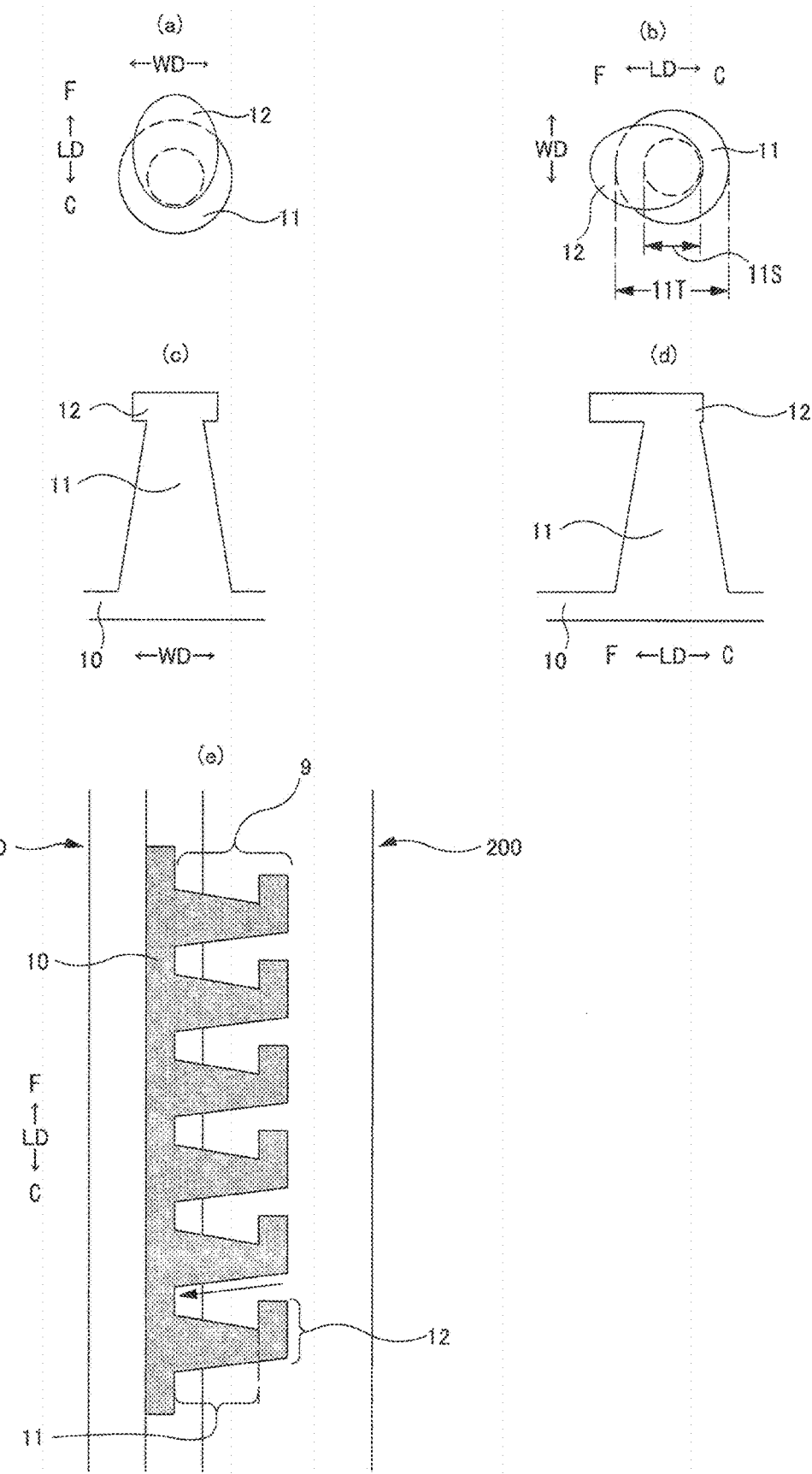

[FIG.11]
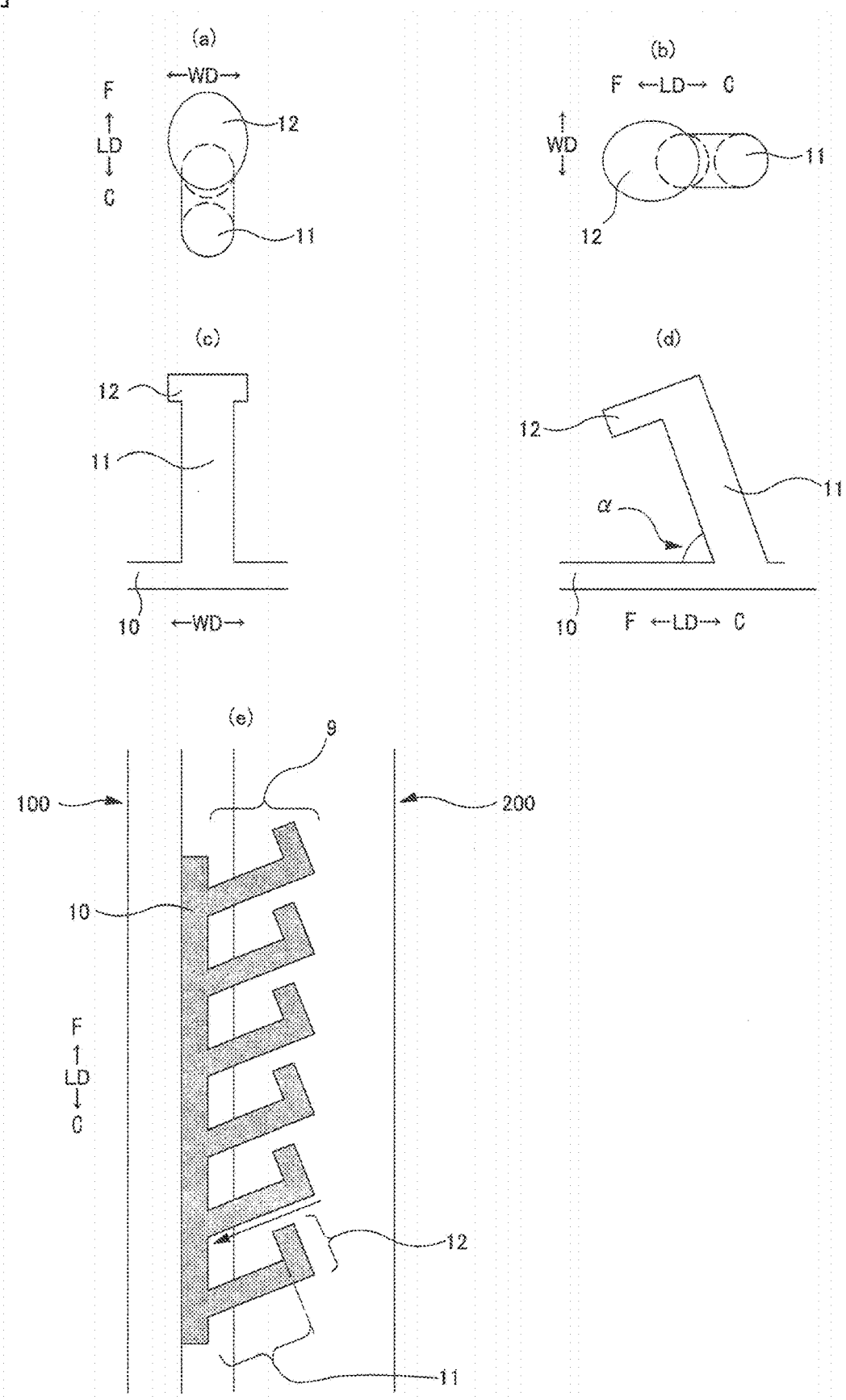

[FIG.12]
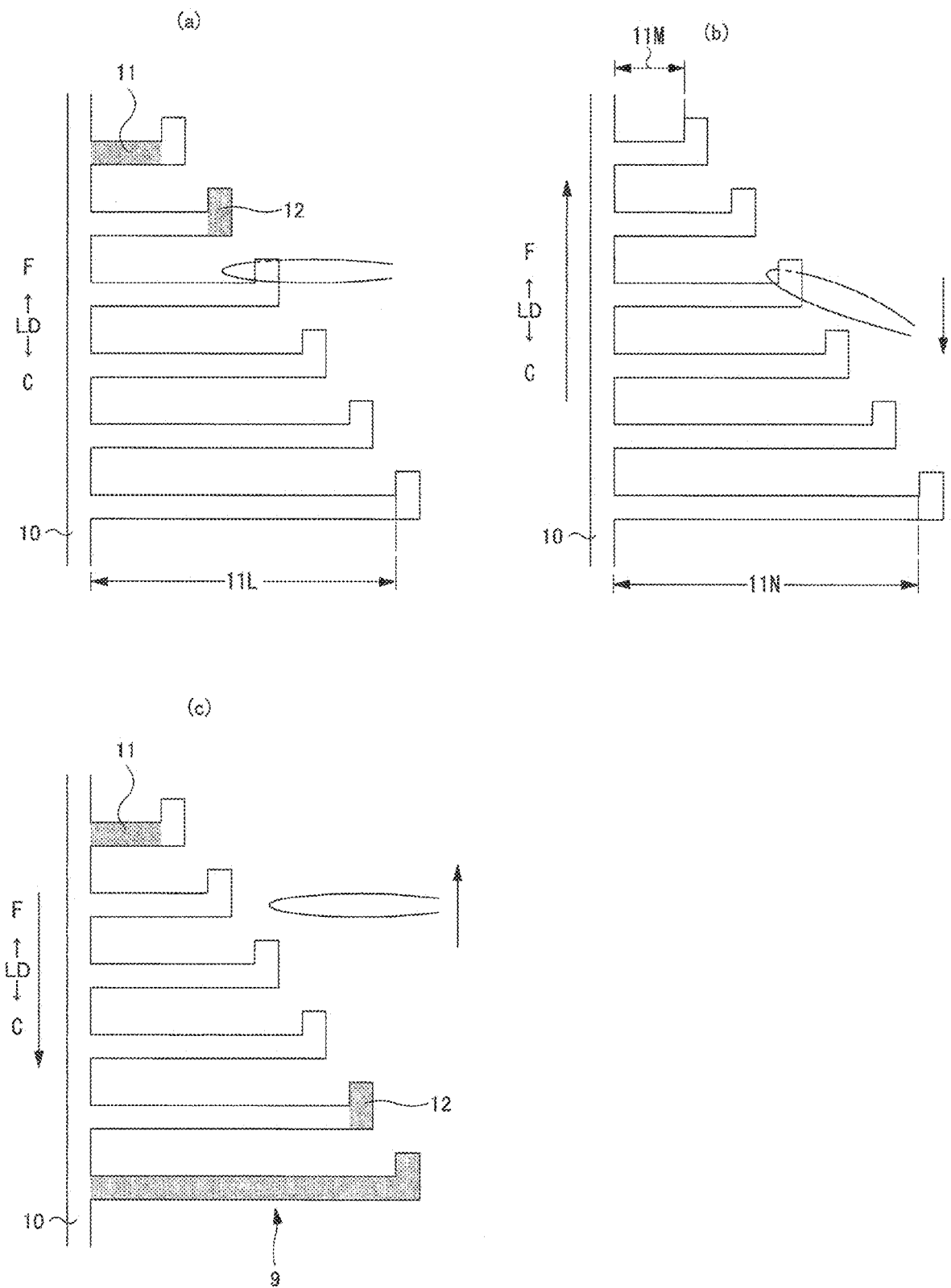

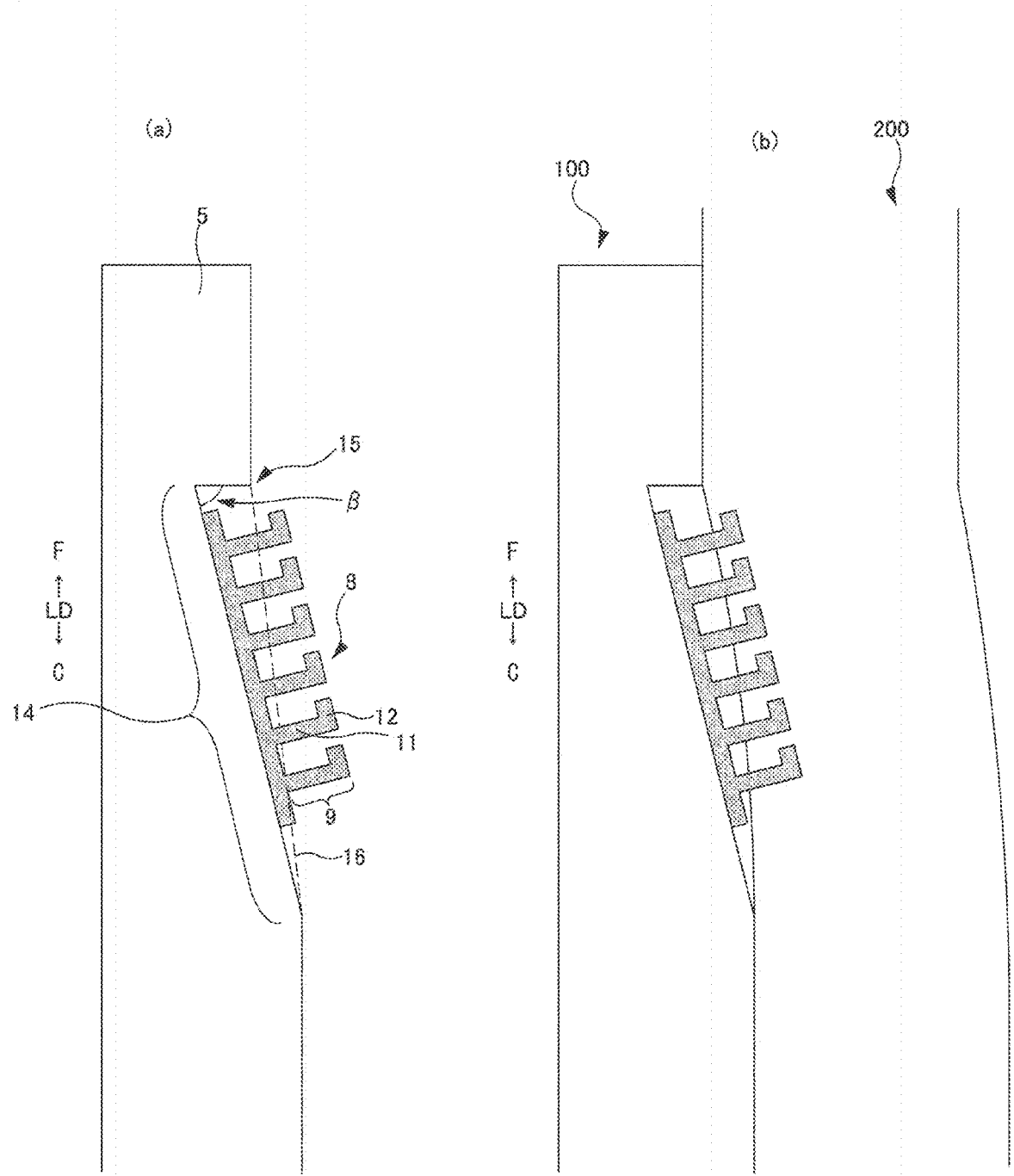
[FIG.13]

[FIG.14]
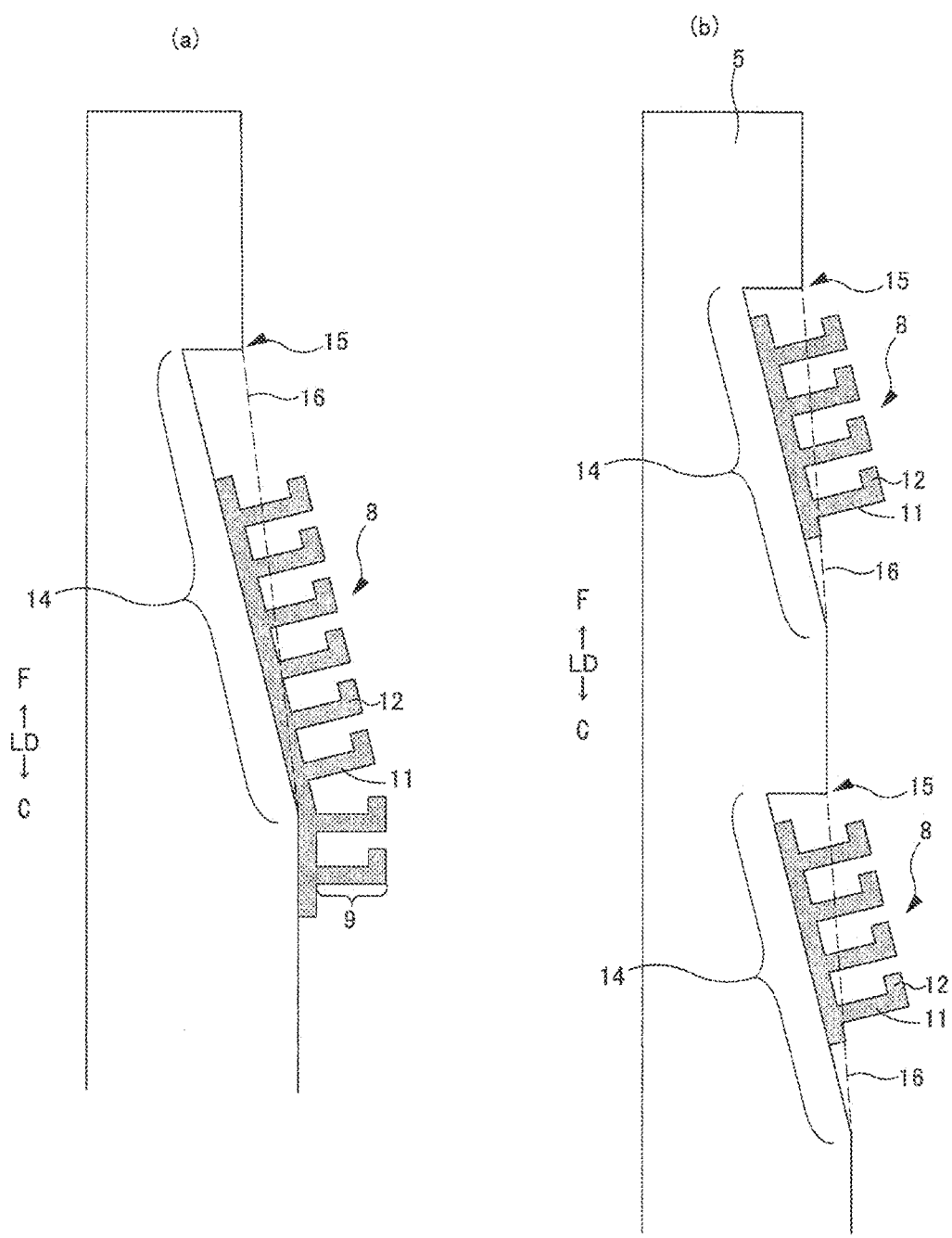

[FIG.15]
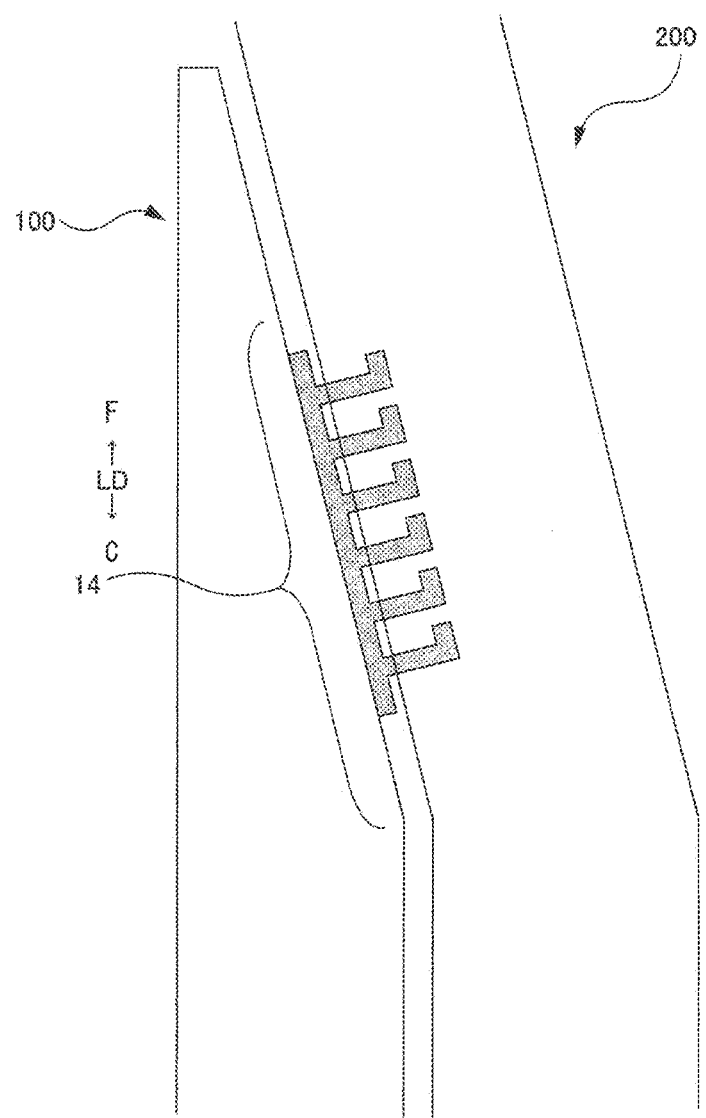

ABSORBENT ARTICLE

CROSS-REFERENCE TO RELATED APPLICATIONS

This application is the U.S. national stage application of International Application PCT/JP2021/019765, filed May 25, 2021, which international application was published on Mar. 17, 2022, as International Publication WO 2022/054347 in the Japanese language. The International Application claims priority of Japanese Patent Application No. 2020-152251, filed Sep. 10, 2020. The international application and Japanese application are both incorporated herein by reference, in entirety.

TECHNICAL FIELD

The present invention relates to an absorbent article such as a pad type or flat type absorbent article.

BACKGROUND ART

An absorbent article such as a pad type or flat type absorbent article (also referred to as a urine absorbing pad) is worn by being applied to a crotch of a wearer from a flat state or a state close thereto, and is different from an underpants-type absorbent article having leg openings in a product state.

In general, a pad type or flat type absorbent article is used by being attached to an outer such as an underpants-type diaper or an undergarment, and a pressure sensitive adhesive tape, a mechanical fastener, or the like is used for the attachment. The pad type or flat type absorbent article is required to be firmly fixed so as not to be displaced from an outer or not to be easily peeled off from the outer by movement of a wearer.

In order to solve this problem, the technique described in Patent Literature 1 is one of effective means. In general, in a hook member of a mechanical fastener, a plurality of hook portions with front-back and left-right symmetrical elliptical caps at ends of vertical axes is aligned on a sheet base material. When the cap is enlarged or the axis is lengthened, the hook member is easily entangled with a loop of a tape member of the mechanical fastener, and an engaging force can be increased. In the technique described in Patent Literature 1, a hook member of a mechanical fastener is used as a fastening member used for attaching a disposable auxiliary pad, which is an absorbent article, to a diaper body, and a hook of the hook member is formed in a width direction of the pad. Therefore, an engaging force in the width direction is strong, and displacement hardly occurs in the width direction. Meanwhile, since the hook of the hook member is not formed in a length direction of the pad, an engaging force is weak, and the hook can be easily removed in the length direction.

CITATION LIST

Patent Literature

Patent Literature 1: JP 2013-000286 A

SUMMARY OF INVENTION

Technical Problem

However, the absorbent article described in Patent Literature 1 has a strong engaging force in the width direction, but has a weak engaging force in the length direction. Therefore, every time a wearer puts on or takes off a diaper to which the absorbent article is attached a plurality of times, the auxiliary pad may be displaced in the front-back direction of the diaper, or a corner of the auxiliary pad may be turned up and the auxiliary pad may be peeled off from the diaper. If the auxiliary pad is displaced every time a wearer puts on or takes off the diaper, the wearer needs to correct the displacement each time, and if the wearer uses the auxiliary pad without correcting the displacement, leakage occurs. In addition, since the hook member is not attached to a distal end portion of the pad on an outer side of the hook member of the mechanical fastener in the length direction, the distal end portion of the pad may float from the diaper. When the diaper is pulled up, the distal end portion of the pad may be caught between a body side of the wearer and the diaper, and the wearer may feel discomfort, or the pad may be turned up and detached from the diaper.

In addition, since the pad generally has a high rigidity, the pad is often fixed while keeping a V-shape, which is a folding line attached at the time of packing, in the diaper, and it is difficult to bring the diaper and the pad into close contact with each other without a gap therebetween without directly touching an inner surface, which is a skin adhesion surface of the diaper, with a hand. Furthermore, if the pad is fixed too firmly, a gap is generated between the pad and the diaper, and easily causes leakage. If the absorbent article is not in close contact with the diaper, the diaper looks bulky, and therefore an appearance of the diaper may be poor. In order to eliminate the gap generated between the pad and the diaper, it is necessary for the wearer to directly touch the skin adhesion surface of the pad with a hand to bring the pad into close contact with the diaper, which is troublesome and unsanitary.

Therefore, a main object of the present invention is to provide a more preferable absorbent article having an attachment member that prevents detachment or displacement of a pad, which is an absorbent article, from a diaper due to a strong engaging force for attaching the pad to the diaper in a direction of pulling up the pad and that brings the pad and the diaper into close contact with each other due to a weak engaging force for attaching the pad to the diaper in a direction of lowering the pad.

Solution to Problem

An absorbent article that has solved the above problem is as follows.

FIRST EMBODIMENT

An absorbent article having a crotch portion, a front side region on a front side of the crotch portion, and a back side region on a back side of the crotch portion,
    including a front surface sheet facing a skin of a wearer, a back surface sheet located on a side opposite to the front surface sheet, and an attachment member which is formed in each of the front side region and the back side region of the back surface sheet, and by means of which the absorbent article can be removably attached to an inner surface of an outer located on an outer side, wherein the attachment member is a hook member of a mechanical fastener,
    the hook member is formed of a sheet-like base portion and a plurality of hook portions, the hook portion has a support column extending from the base portion and a protruding portion at an end of the support column on the base portion, in each of the large number of hook portions located in the front side region, the protruding portion extends in a front-back direction, and the length of a front side of the protruding portion is longer than the length of a back side of the protruding portion, or the protruding portion extends to a front side in the front-back direction, and in each of the large number of hook portions located in the back side region, the protruding portion extends in the front-back direction, and the length of a back side of the protruding portion is longer than the length of a front side of the protruding portion, or the protruding portion extends to a back side in the front-back direction.

(Action and Effect)

When the present absorbent article is attached to an outer such as an underpants-type diaper or a cloth diaper via the attachment member, which is a hook member of a mechanical fastener, the strength and the directionality of an engaging force can be adjusted by the protruding portions of the plurality of hook portions aligned in the hook member. When the present absorbent article is attached to an outer such as an underpants-type diaper via the attachment member, the hook member as the attachment member has a protruding portion that is long upward in the front-back direction and short downward in the front-back direction, or has a protrusion extending only upward in the front-back direction. Therefore, an engaging force is strong upward in the front-back direction and is weak downward in the front-back direction. In a case where such a hook member is disposed, when a wearer pulls up the diaper, an upward force in the front-back direction is applied to the absorbent article. Therefore, the protruding portion extending upward in the front-back direction is entangled with a nonwoven fabric fiber of an outer such as the diaper, and an upward engaging force of the present absorbent article is strong. Therefore, displacement hardly occurs. When the wearer puts the body in the diaper, a downward force in the front-back direction is applied to the absorbent article, and there is a short protruding portion or no protruding portion downward in the front-back direction. Therefore, the protruding portion is hardly entangled or never entangled with the nonwoven fabric of the diaper, the present absorbent article is more likely to slide downward so as to be in close contact with the outer such as the diaper, there is no need to touch a front surface sheet and correct displacement at the time of wearing, and leakage from a gap between the diaper and the absorbent article is less likely to occur. In addition, since the diaper and the present absorbent article are in close contact with each other, the diaper does not look bulky and has a good appearance, and the wearer is less likely to feel discomfort at the time of wearing.

SECOND EMBODIMENT

The absorbent article according to the first embodiment, wherein the support column of the hook portion becomes thinner as it goes from the base portion toward the protruding portion.

(Action and Effect)

In the hook member of the mechanical fastener as the attachment member of the first embodiment, by forming the support column of the hook portion in a shape that becomes thinner as it goes from the sheet-like base portion toward the protruding portion, the support column is inclined. Therefore, a nonwoven fabric fiber of an outer such as a diaper engaged with the hook member of the mechanical fastener moves in a direction of the sheet-like base portion at a root of the support column along the inclination of the support column, the present absorbent article slides downward in the front-back direction more easily than that in the first embodiment, and the diaper and the present absorbent article are brought into close contact with each other more easily without trouble of correction.

THIRD EMBODIMENT

The absorbent article according to the first embodiment, wherein the support column of the hook portion extends from the base portion as a start point, the support column extends from a crotch portion side to a front side in the hook portion located in the front side region, and the support column extends from the crotch portion side to a back side in the hook portion located in the back side region.

(Action and Effect)

When the present absorbent article is attached to an outer such as a diaper, the support column of the hook portion of the hook member of the mechanical fastener as the attachment member extends obliquely upward in the front-back direction from the sheet-like base portion toward the protruding portion. As a result, the support column of the hook portion is attached to the diaper while maintaining the inclination, and a nonwoven fabric fiber of the diaper engaged with the hook member easily slides downward in the front-back direction along the oblique support column of the hook portion to the sheet-like base portion at a root of the support column. Furthermore, since the longer protruding portion extending from an end of the support column is easily stuck into the nonwoven fabric upward in the front-back direction, the engaged nonwoven fabric fiber is less likely to be released from the hook portion than that in the second embodiment. Since the present absorbent article has a strong engaging force upward in the front-back direction and a weak engaging force downward in the front-back direction, the absorbent article is hardly detached or peeled off when the diaper is put on or taken off, and is more preferable than a case where the absorbent article is in close contact with the diaper when the diaper is worn.

FOURTH EMBODIMENT

The absorbent article according to the first embodiment, wherein in the mechanical fastener attached to the front side region, the length of the support column of the hook portion located on a front side is getting shorter, and the length of the support column of the hook portion located on a crotch portion side is getting longer, and in the mechanical fastener located in the back side region, the length of the support column of the hook portion located on a back side is getting shorter, and the length of the support column of the hook portion located on the crotch portion side is getting longer.

(Action and Effect)

In the present embodiment, the length of the support column of the hook portion of the hook member becomes shorter as it goes from the crotch portion side toward the distal end portion side, which is the front side region distal end or the back side region distal end. Therefore, the positions of the protruding portions at the ends of the support columns are not aligned so as to be adjacent to each other on a longitudinal straight line in the front-back direction and are aligned obliquely in the front-back direction. In a case where an upward force in the front-back direction is applied to the present absorbent article when the present absorbent article is attached to an outer such as a diaper, a nonwoven fabric fiber of the diaper entangled with the protruding portion is displaced in a root direction of the protruding portion or the support column and stops. Therefore, engagement is more likely to be maintained. Meanwhile, in a case where a downward force in the front-back direction is applied to the present absorbent article, a nonwoven fabric fiber entangled with the hook portion is displaced in a distal end direction of the protruding portion and released from the protruding portion. At an end from which the nonwoven fabric fiber has been released, there is no adjacent protruding portion because the lengths of the support columns of the hook portion are different from each other, and the detached nonwoven fabric fiber is less likely to be engaged with another protruding portion of the hook portion and remains released. Therefore, in this structure, downward engagement in the front-back direction is less likely to occur. That is, the present absorbent article serves as a hook member that is strong against displacement upward in the front-back direction and is slippery downward in the front-back direction. When a wearer takes off a diaper to which the present absorbent article is attached, the present absorbent article is less likely to be detached or displaced from the diaper. When the wearer puts on a diaper to which the present absorbent article is attached, the present absorbent article is brought into close contact with the diaper. Therefore, leakage is prevented, and discomfort at the time of wearing is less likely to occur.

FIFTH EMBODIMENT

The absorbent article according to the first embodiment, wherein a recess is formed in the front-back direction in each of the front side region and the back side region of the back surface sheet,
the recess in the front side region is formed so as to be deeper on a front side than on a crotch portion side,
a convex high in a thickness direction is formed at a front side end of the recess,
the recess in the back side region is formed so as to be deeper on a back side than on the crotch portion side,
a convex high in the thickness direction is formed at a back side end of the recess,
the hook member in which the lengths of the support columns of the hook portions are equal to each other is fixed to the recess, and
the support columns of the hook member are present on a line connecting a start point of the recess located on the crotch portion side and a vertex of the convex in the front-back direction.
(Action and Effect)

By forming a recess that becomes deeper as it goes toward a distal end portion side, which is a front side region distal end or a back side region distal end, at a position where the attachment member of the back surface sheet of the present absorbent article is attached by embossing or the like, and forming an inclination such that a crotch portion side is shallow and the distal end portion side is deep in the front-back direction, the hook member of the mechanical fastener is bonded to the present absorbent article in an inclined manner. In addition, by forming a high convex in a thickness direction of the absorbent article at an end point of the recess located on the distal end portion side where the recess is deepest, the hook member of the mechanical fastener can be attached such that the support columns of the hook portions of the hook member of the mechanical fastener are located on a line connecting a vertex of the convex and a start point of the recess on the crotch portion side. In addition, a diaper or the like as an outer is brought into contact with the convex high in the thickness direction on the distal end portion side. This prevents the diaper from closely following the inclination due to the recess of the present absorbent article, and the hook member is attached to the nonwoven fabric of the diaper as an outer in an inclined manner such that the length of the support column of the hook portion of the hook member actually entangled with a nonwoven fabric fiber of the diaper is long on the crotch portion side and is short on the distal end portion side even if the length itself of the support column of the hook portion of the hook member of the mechanical fastener is constant. As a result, even if a hook member in which the lengths of the support columns of the hook portion are different from each other, such as the hook member of the mechanical fastener of the fourth embodiment, is not prepared, by attaching the hook member having the support columns of the hook portions of the same length to the inclination generated by the recess, the length of the support column entangled with a nonwoven fabric is longest on the crotch portion side and becomes shorter as it goes upward in the front-back direction, which is the distal end portion side. Therefore, the same action and effect as the fourth embodiment can be obtained.

Advantageous Effects of Invention

The present invention provides an absorbent article that is hardly peeled off or displaced when a wearer repeatedly takes off an outer such as a diaper to which the absorbent article is attached because the absorbent article is strong against a force applied upward in the front-back direction to the absorbent article, and that slides downward and is brought into close contact with the diaper without correction when the wearer puts on the diaper to which the absorbent article is attached because the absorbent article is weak against a force applied downward in the front-back direction to the absorbent article.

BRIEF DESCRIPTION OF DRAWINGS

FIG. 1(*a*) is a plan view (internal surface side) of an absorbent article according to the present invention, FIG. 1(*b*) is a plan view of an external surface side of FIG. 1(*a*), and FIG. 1(*c*) is a cross-sectional view taken along line 1-1.

FIG. 2 is another plan view (external surface side) illustrating a mechanical fastener of the absorbent article according to the present invention.

FIG. 3 is a cross-sectional view taken along line 2-2.

FIG. 4 is another cross-sectional view taken along line 2-2.

FIG. 5 is a perspective view illustrating a manner of attaching the absorbent article according to the present invention to an outer.

FIG. 6(*a*) is a cross-sectional view of an absorbent article according to related art when being attached to an outer, and FIG. 6(*b*) is a cross-sectional view of the absorbent article according to the present invention when being attached to an outer.

FIG. 7(*a*) is a perspective view of a mechanical fastener of an absorbent article according to a first embodiment, and FIG. 7(*b*) is a plan view of FIG. 7(*a*).

FIGS. 8(*a*) and 8(*b*) are plan views of a hook portion according to the first embodiment, FIG. 8(*c*) is a front view of the hook portion as viewed in a width direction, FIG. 8(*d*) is a front view of the hook portion as viewed in a front-back direction, and FIG. 8(*e*) is a cross-sectional view of the mechanical fastener in the front-back direction.

FIGS. 9(*a*) and 9(*b*) are other plan views of the hook portion according to the first embodiment, FIG. 9(*c*) is another front view of the hook portion as viewed in a width direction, FIG. 9(*d*) is another front view of the hook portion as viewed in a front-back direction, and FIG. 9(*e*) is another cross-sectional view of the mechanical fastener in the front-back direction.

FIGS. 10(*a*) and 10(*b*) are plan views of a hook portion according to a second embodiment, FIG. 10(*c*) is a front view of the hook portion as viewed in a width direction, FIG. 10(*d*) is a front view of the hook portion as viewed in a front-back direction, and FIG. 10(*e*) is a cross-sectional view of a mechanical fastener in the front-back direction.

FIGS. 11(*a*) and 11(*b*) are plan views of a hook portion according to a third embodiment, FIG. 11(*c*) is a front view of the hook portion as viewed in a width direction, FIG. 11(*d*) is a front view of the hook portion as viewed in a front-back direction, and FIG. 11(*e*) is a cross-sectional view of a mechanical fastener in the front-back direction.

FIG. 12(*a*) is a schematic diagram illustrating an engaged state between a hook portion according to a fourth embodiment and a nonwoven fabric fiber, FIG. 12(*b*) is a schematic diagram when a force is applied to the hook portion in a longitudinally upward direction, and FIG. 12(*c*) is a schematic diagram when a force is applied to the hook portion in a longitudinally downward direction.

FIG. 13(*a*) is a cross-sectional view of the vicinity of an attachment portion of an absorbent article according to a fifth embodiment, and FIG. 13(*b*) is a cross-sectional view of the vicinity of an attachment portion between the absorbent article and an outer.

FIG. 14 is another cross-sectional view of the vicinity of the attachment portion of the absorbent article according to the fifth embodiment.

FIG. 15 is another cross-sectional view of the vicinity of the attachment portion between the absorbent article according to the fifth embodiment and an outer.

DESCRIPTION OF EMBODIMENTS

Hereinafter, an example of an absorbent article will be described in detail with reference to the attached drawings.

FIGS. 1 and 2 illustrate an absorbent article. These drawings illustrate a pad type or flat type absorbent article, but the present invention is not limited to the following embodiments. A hook member 8 and a hook portion 9 of a mechanical fastener illustrated in FIGS. 7 to 15 illustrate a state in a front side region F. Description will be made below assuming that a hook member 8 and a hook portion 9 of a mechanical fastener in a back side region B are also illustrated in similar drawings, although not illustrated.
(Structure Example of Absorbent Article)

As illustrated in FIGS. 1, 3, and 4, an absorbent article has a structure in which an absorber 6 is interposed between a top sheet 4 as a front surface sheet and a back sheet 5 as a back surface sheet, and absorbs and holds an excretory liquid that has passed through the top sheet 4 into the absorber 6. The back sheet 5 includes, in each of the front side region F and the back side region B, a hook member 8 of a mechanical fastener, which is an attachment member for detachably fastening the absorbent article of the present invention to an outer such as an underpants-type diaper or a garment. The planar shape of the absorbent article is not particularly limited, but is, in general, approximately rectangular as illustrated in the embodiment of FIG. 1. As illustrated in FIGS. 1(*a*), 1(*b*), and 2, the four corners may be cut off or do not have to be cut off.

As the top sheet 4 covering a front surface side (skin contact surface side) of the absorber 6, a perforated or non-perforated nonwoven fabric, a porous plastic sheet, or the like is preferably used. Examples of a material fiber constituting the nonwoven fabric include a synthetic fiber such as a polyolefin-based fiber including polyethylene and polypropylene, a polyester-based fiber, or a polyamide-based fiber, a regenerated fiber such as rayon or cupra, and a natural fiber such as cotton. A nonwoven fabric obtained by an appropriate processing method such as a spunlace method, a spunbond method, a thermal bond method, a melt blown method, or a needle punch method can be used. Among these processing methods, the spunlace method is excellent from viewpoints of high flexibility and drapeability, and the thermal bond method is excellent from viewpoints of bulkiness and softness. When a large number of through-holes are formed in the top sheet 4, urine or the like is quickly absorbed.

The back sheet 5 covering a back surface side (non-skin contact surface side) of the absorber 6 may be liquid pervious similarly to the top sheet 4 or liquid impervious. When the back sheet 5 is liquid impervious, a liquid impervious plastic sheet such as polyethylene or polypropylene is used. However, in recent years, a moisture permeable sheet is preferably used from a viewpoint of preventing stuffiness. As the water blocking and moisture permeable sheet, a microporous sheet obtained by melt-kneading inorganic fine particles such as calcium carbonate in a polyolefin resin such as polyethylene or polypropylene to form a sheet, and then stretching the sheet in a monoaxial or biaxial direction can be preferably used.

The absorber 6 may have a single layer structure as illustrated in FIGS. 1(*c*), 3, and 4, or may have a structure including a plurality of layers.

As the absorber 6, a known absorber, for example, a pulp fiber stack, an assembly of filaments such as cellulose acetate, or a nonwoven fabric can be basically used. Alternatively, an absorber obtained by, for example, mixing and fixing a super absorbent polymer as necessary can be used.

The absorber 6 can be wrapped by a wrapping sheet having liquid perviousness and a liquid holding property, such as crepe paper, as necessary, for example, for holding the shape and a polymer.

In FIG. 1(*a*), the absorber 6 is formed in an hourglass shape having a narrowing portion narrower than each of front and back sides in a crotch portion C, but can have an appropriate shape such as a rectangular shape.

As illustrated in FIGS. 1(*a*), 1(*c*), and 5, a three-dimensional gather BS that mainly fits a periphery of a leg may be formed on each side portion of the top sheet 4. As illustrated in FIG. 1(*c*), the three-dimensional gather BS includes a side edge portion fixed to each side portion of the top sheet 4 of the absorbent article, and a free portion extending from the side edge portion inward in a width direction WD of the top sheet 4 and freely moving in a non-fixed manner. The side edge portion extends to a back surface of the back sheet 5, and an elongated gather elastic member 7 is disposed in the side edge portion. An elongated gather elastic member 7 is also disposed at a distal end portion of the free portion. In the three-dimensional gather BS, the free portion protruding from the side edge portion of the top sheet 4 rises in a product state due to contraction of the gather elastic member 7.

As the three-dimensional gather BS, a water-repellent nonwoven fabric is preferably used. The shape and presence or absence of the three-dimensional gather BS, the shape of the side edge portion, and the number and positions of the gather elastic members 7 are not limited to those of the present embodiment, and can be appropriately determined.

As the gather elastic member 7, a usually used material such as a polystyrene-based rubber, a polyolefin-based rubber, a polyurethane-based rubber, a polyester-based rubber, polyurethane, polyethylene, polystyrene, a styrene-butadiene copolymer, silicone, or polyester can be used.

In order to make it difficult to see the gather elastic member 7 from the outside, the gather elastic member 7 preferably has a fineness of 925 dtex or less, a tension of 150 to 350%, and an interval of 7.0 mm or less. Note that as the gather elastic member 7, a tape-like member having a certain width can be used in addition to a thread-like member as in the illustrated embodiment.

Similarly to the top sheet 4, as a material fiber constituting the above-described three-dimensional gather BS, in addition to a synthetic fiber such as a polyolefin-based fiber including polyethylene and polypropylene, a polyester-based fiber, or a polyamide-based fiber, a regenerated fiber such as rayon or cupra, and a natural fiber such as cotton can be used. A nonwoven fabric obtained by an appropriate processing method such as a spunbond method, a thermal bond method, a melt blown method, or a needle punch method can be used. Particularly, a nonwoven fabric having a reduced basis weight and excellent air permeability is preferably used in order to prevent stuffiness. Furthermore, as a gather sheet, in order to prevent urine or the like from passing through the gather sheet, to prevent rash, and to enhance feeling (dry feeling) to a skin, it is desirable to use a water repellent nonwoven fabric coated with, for example, a silicone-based, paraffin metal-based, or alkylchromic chloride-based water repellent agent.

(Structure of Hook Portion of Absorbent Article)

When the absorbent article is cut along line 2-2 in a front-back direction LD, as illustrated in FIGS. 3 and 4, there is the hook member 8 of the mechanical fastener as an attachment member for fastening the present absorbent article to an outer in each of the front side region F and the back side region B of the back sheet 5. In FIGS. 1(b) and 5, the hook member 8 has a rectangular shape long in the width direction WD. However, as illustrated in FIG. 2, the number, shapes, and attachment positions of the hook members to be attached can be appropriately determined within the range of the front side region F and the back side region B. The front side region F can be a range from a position of 0.10Y (Y is the maximum length of the product) on a front side based on the center of the product in the front-back direction LD to a front end portion. The back side region B can be a range from a position of 0.10Y on a back side based on the center to a back end portion. The crotch portion C can be a range therebetween. More desirably, the front side region F is present within a range from a position of 0.30Y on a front side based on the center of the product in the front-back direction LD to a front end portion, and the back side region B is present within a range from a position of 0.30Y on a back side based on the center of the product in the front-back direction LD to a back end portion.

As illustrated in the enlarged views of FIGS. 3 and 6 and FIGS. 7 to 15, the hook member 8 of the mechanical fastener is formed of a sheet-like base portion 10 and a large number of hook portions 9 extending from the base portion 10 in a direction opposite to the back sheet 5. The hook portion 9 has a support column 11 extending from the base portion 10 in the direction opposite to the back sheet 5 and a protruding portion 12 located at an end of the support column 11 on the sheet-like base portion 10. The protruding portion 12 may be formed by being combined with or bonded to the support column 11 as a separate component, or may be formed integrally with the support column 11.

As illustrated in FIG. 8, the protruding portion 12 has a shape in which a protrusion extends in the front-back direction LD, and a length 12S of the protrusion on the crotch portion C side is shorter than a length 12L of the protruding portion on the distal end portion side of each of the front side region F and the back side region B (12L>12S), or a shape in which the protruding portion 12 extends only to the distal end portion side of each of the front side region F and the back side region B as illustrated in FIG. 9. In addition, the protruding portion 12 preferably has a shape in which a length 12W in the width direction illustrated in FIG. 8(a) is shorter than the length 12L of the protruding portion on the distal end portion side of each of the front side region F and the back side region B illustrated in FIGS. 8(d) and 9(d) and longer than the length 12S of the protrusion on the crotch portion C side (12L>12W>12S) in order to exhibit an engaging force in the width direction and prevent displacement of the absorbent article in the width direction. The protruding portion 12 illustrated in FIG. 8(b) has a maximum length 12T in the front-back direction LD of 100 to 500 μm, preferably 150 to 300 μm, and a maximum length 12W in the width direction WD of 90% or less, preferably 70% or less of the maximum length 12T in the front-back direction LD. The length 12L of the protruding portion 12 on the distal end portion side of each of the front side region F and the back side region B is 5 to 20%, preferably 10 to 20% of the maximum length 12T in the front-back direction LD. The length 12S of the protruding portion 12 on the crotch portion C side is 15% or less, preferably 5% or less of the maximum length 12T in the front-back direction LD. A diameter 11D of the support column 11 illustrated in FIG. 8(b) is 100 to 300 μm, preferably 150 to 250 μm. A length 11L of the support column 11 illustrated in FIG. 8(c) is 100 to 500 μm, preferably 250 to 450 μm. However, the maximum length 12T of the protruding portion 12 in the front-back direction LD, the maximum length 12W of the protruding portion 12 in the width direction WD, the lengths 12L and 12S of the protruding portion extending in the front-back direction LD, and the diameter 11D and the length 11L of the support column 11 are appropriately determined by the shape of the hook portion 9, and are not limited to the above-described lengths. The shape of the hook portion 9 in FIG. 3 is an L shape, but is not limited to the L shape, and may be any shape such as a J shape or a T shape.

As illustrated in FIG. 5, the present absorbent article 100 is used by being attached to an inner surface of an outer 200 such as an underpants-type diaper or a garment. In a protruding portion of a hook member of a usual mechanical fastener as illustrated in FIG. 6(a), which is often used, protrusions extend by substantially the same length to the distal end portion side of each of the front side region F and the back side region B, which is upward in the front-back direction LD, and to the crotch portion C side, which is downward in the front-back direction LD. Therefore, a nonwoven fabric fiber of a diaper 200 and the protruding portion of the absorbent article 100 are entangled with each other and engaged with each other both upward and downward in the front-back direction LD. When the nonwoven fabric fiber of the diaper 200 and the protruding portion of the absorbent article 100 are engaged with each other in the front-back direction LD, the absorbent article 100 is fixed and attached to the diaper 200. However, the absorbent article itself may have a strong rigidity. When the absorbent article is only attached to the diaper, as illustrated in FIG. 6(*a*), the absorbent article still has a folding line 17 generated at the time of packing, and the absorbent article is attached while maintaining the V-shape. Therefore, the absorbent article 100 does not follow the diaper 200 to generate a gap 13 between the diaper 200 and the absorbent article 100 in some cases. In this case, leakage may occur from the gap 13 between the diaper 200 and the absorbent article 100, or displacement of the absorbent article at the time of wearing may occur.

The hook member 8 of the mechanical fastener of the present absorbent article 100 has a shape in which a protrusion of the protruding portion 12 of the hook portion 9 is short on the crotch portion C side in the front-back direction LD as illustrated in FIG. 8, or there is no protrusion of the protruding portion 12 of the hook portion 9 on the crotch portion C side in the front-back direction LD, and the length of the protruding portion 12 of the hook portion 9 is long in the distal end portion direction of each of the front side region F and the back side region B as illustrated in FIGS. 6(*b*) and 9. That is, the hook member 8 of the present absorbent article 100 is formed of the large number of hook portions 9 having a strong engaging force in the distal end portion direction of each of the front side region F and the back side region B, which is upward in the front-back direction LD, and a weak engaging force on the crotch portion C side, which is downward in the front-back direction LD. Therefore, when a force upward in the front-back direction LD is applied to the absorbent article 100, for example, by taking off or putting on the diaper, the absorbent article 100 and the diaper 200 are less likely to be displaced from each other. When a force downward in the front-back direction LD is applied to the absorbent article 100 by wearing the diaper 200, the absorbent article 100 slides downward in the front-back direction LD together with the body to follow the shape of the diaper 200. Therefore, even in a case of the absorbent article 100 having a rigidity, the absorbent article 100 is turned into a state following the diaper 200 at the time of wearing from a V-shaped state at the time of attachment, the gap 13 between the diaper 200 and the absorbent article 100 as illustrated in FIG. 6(*a*) is less likely to be generated, and occurrence of leakage or occurrence of displacement or peeling at the time of wearing is less likely to occur.

(Example of Hook Portion of Absorbent Article)

FIG. 8 illustrates a first example. The large number of hook portions 9 each formed of the protruding portion 12 having the long length 12L on the distal end portion side of each of the front side region F and the back side region B and the short length 12S on the crotch portion C side are gathered to form the hook member 8.

Since the length 12L on the distal end portion side of each of the front side region F and the back side region B is long and the length 12S on the crotch portion C side is short (12L>12S), the hook member 8 has a strong engaging force on the distal end portion side and a weak engaging force on the crotch portion C side, and the absorbent article is strong against displacement upward in the front-back direction LD and easily moves downward in the front-back direction LD. As a result, when an outer such as a diaper to which the absorbent article is attached is taken off, the absorbent article is less likely to be displaced or peeled off even if a force upward in the front-back direction LD is applied to the attached absorbent article. When the diaper to which the absorbent article is attached is put on, the absorbent article slides following the diaper with movement of the body even if a force downward in the front-back direction LD is applied. Therefore, the absorbent article and the outer are in close contact with each other, leakage from a gap between the absorbent article and the diaper is less likely to occur, a wearing feeling of a wearer is improved, and stiffness in appearance is reduced. Since the absorbent article is brought into close contact with the diaper with movement of the body, it is not necessary to directly touch and bring the top sheet 4 into close contact with the diaper with a hand at the time of wearing, which is also hygienic.

FIG. 9 illustrates another aspect of the first example. In this aspect, the protruding portion 12 has a shape in which a protrusion extends only to the distal end portion side of each of the front side region F and the back side region B and there is no protrusion on the crotch portion C side. In this shape, since the crotch portion C side, which is downward in the front-back direction LD, is extremely less likely to be entangled with a nonwoven fabric fiber of an outer such as a diaper is very low, there is no downward engaging force in the front-back direction LD, sliding of the absorbent article downward in the front-back direction LD more easily occurs than in the first example, and the absorbent article is more easily brought into close contact with the diaper.

FIG. 10 illustrates a second example, in which the support column 11 of the hook portion 9 becomes narrower as it goes from the base portion 10 toward the protruding portion 12. The support column 11 is inclined by changing the thickness of the support column 11. Therefore, when the hook member 8 is attached to an outer such as a diaper, a nonwoven fabric fiber is entangled with the protruding portion 12 of the hook portion 9, and the entangled fiber may easily slide in the direction of the base portion 10 along the inclination of the support column 11. Therefore, movement of the absorbent article to the crotch portion C side, which is downward in the front-back direction LD, easily occurs, and the absorbent article is more likely to be smoothly brought into close contact with the diaper with movement of the body than in the first example.

Regarding the thickness of the support column illustrated in FIG. 10(*b*), a diameter 11T at the base portion 10, which is the thickest portion of the support column 11, is 200 to 500 μm, preferably 300 to 400 μm, and a diameter 11S at the protruding portion 12, which is the thinnest portion, is 50 to 90%, preferably 60 to 75%, of the diameter 11T at the base portion 10, which is the thickest portion. The diameter lengths 11T and 11S can be appropriately determined, and are not limited.

In the third example illustrated in FIG. 11, the support column 11 of the hook portion 9 extends upward in the front-back direction LD from the base portion 10 toward the protruding portion 12. Since the hook portion 9 is engaged such that the protruding portion 12 is stuck into an outer such as a diaper, engagement in the distal end portion direction of each of the front side region F and the back side region B, which is upward in the front-back direction LD, is strong. Since the support column 11 extends obliquely, a nonwoven fabric fiber entangled with the hook portion 9 easily slides in the direction of the base portion 10 of the hook portion 9 along the oblique support column 11. The third example is more preferable than the first and second examples because upward engagement in the front-back direction LD is strong, and sliding downward in the front-back direction LD easily occurs.

An angle α between a front side of the sheet-like base portion 10 in the front-back direction LD and the support column 11 illustrated in FIG. 11(*d*) is 60 to 88 degrees, preferably 70 to 85 degrees, but the angle can be appropriately determined and is not limited.

A fourth example d of FIG. 12 illustrates the shape of a hook member 8 of a mechanical fastener in an absorbent article having hook portions 9 in which the length 11L of a support column 11 is long on the crotch portion C side and is short on the distal end portion side of each of the front side region F and the back side region B. FIG. 12(*a*) is a diagram in which the hook portion 9 is engaged with a nonwoven fabric fiber of an outer such as a diaper. As illustrated in FIG. 12(*b*), when an upward force in the front-back direction LD is applied to the hook member 8, the engaged nonwoven fabric fiber of the diaper moves from the protruding portion 12 of the hook portion 9 toward the support column 11, and the hook portion 9 and the nonwoven fabric fiber of the diaper are firmly engaged with each other. Meanwhile, as illustrated in FIG. 12(*c*), when a downward force in the front-back direction LD is applied to the hook member 8, the engaged nonwoven fabric fiber is released and detached from the protruding portion 12 of the hook portion 9. Since the length 11L of the support column 11 of the hook portion 9 adjacent upward in the front-back direction LD is shorter than the length 11L of the support column 11 of the hook portion 9 with which the nonwoven fabric fiber was engaged, and the adjacent protruding portion 12 is not present nearby, the nonwoven fabric fiber released and detached from the protruding portions 12 is less likely to be entangled with the protruding portion 12 of the adjacent hook portion 9, and the absorbent article is more likely to slide downward in the front-back direction LD. As described above, since the length 11L of the support column 11 is long on the crotch portion C side and short on the distal end portion side of each of the front side region F and the back side region B, the positions of the protruding portions 12 of the hook portions 9 aligned in the front-back direction LD are directed from the crotch portion C side to the distal end portion side of each of the front side region F and the back side region B, do not overlap each other on a longitudinal straight line in the front-back direction LD, and are aligned obliquely with respect to the front-back direction LD. As a result, the protruding portion 12 is less likely to be engaged with the nonwoven fabric fiber downward in the front-back direction LD, and sliding is more likely to occur downward in the front-back direction LD. This shape is strong against upward displacement in the front-back direction LD and easily causes downward sliding in the front-back direction LD.

In the fourth example, a length 11N, which is the longest length 11L of the support column 11 illustrated in FIG. 12(*b*), is 300 to 500 µm, preferably 350 to 450 µm, and a length 11M, which is the shortest length of the support column 11, is 50 to 95%, preferably 65 to 80% of the longest length 11N. The lengths 11N and 11M of the support column 11 can be appropriately determined, and are not limited. In addition, the hook member 8 of the mechanical fastener in the absorbent article may have hook portions 9 in which the length 11L of the support column 11 is long on the distal end portion side of each of the front side region F and the back side region B side and is short on the crotch portion C side.

(Shape of Recess)

As illustrated in FIGS. 13 to 15, a recess 14 for attaching a hook member 8 of a mechanical fastener is formed in each of the front side region F and the back side region B of the back sheet 5, which is a back surface sheet of an absorbent article 100 of a fifth example, and the absorbent article 100 is inclined by the recess 14, whereby the hook member 8 can be attached obliquely. The recess 14 is shallow on the crotch portion C side, and deepens as it goes toward the distal end portion side of each of the front side region F and the back side region B. A convex 15 high in the thickness direction of the absorbent article 100 is formed at an end point of a portion where the recess 14 is deepest. As illustrated in FIG. 14(*a*), the recess 14 may have any size as long as at least a part of the hook member 8 is obliquely attached, and the size is not particularly limited. The recess 14 may be formed by embossing or cutting the absorbent article 100, and a method for forming the recess 14 is not limited. An angle β between the recess 14 and the convex 15 illustrated in FIG. 13(*a*) is 60 to 88 degrees, preferably 70 to 85 degrees, but the angle can be appropriately determined and is not limited. The number of recesses is not limited, and a plurality of the recesses 14 may be formed in each of the front side region F and the back side region B as illustrated in FIG. 14(*b*). In addition, the recess 14 may be shallow on the distal end portion side of each of the front side region F and the back side region B, and may deepen as it goes toward the crotch portion C side. The convex 15 high in the thickness direction may be formed at an end point of a portion where the recess 14 is deepest.

In the fifth example, as illustrated in FIG. 13(*a*), when the hook member 8 of the mechanical fastener is attached to the recess 14, the support column 11 is located so as to intersect with an auxiliary line 16 connecting a start point of the recess 14 and a vertex of the convex 15, and the protruding portions 12 at ends of the support columns 11 are aligned obliquely with respect to the front-back direction LD. In this state, when the absorbent article 100 is attached to the outer 200 such as a diaper, as illustrated in FIG. 13(*b*), the diaper 200 is attached obliquely to the support column 11 of the hook member 8 of the absorbent article 100, and even if the hook member 8 in which the lengths of the support columns 11 of the hook portions 9 are different from each other as in the fourth example is not prepared, by attaching the hook member 8 in which the length of the support column 11 is constant to the recess 14, as in the fourth example illustrated in FIG. 12, the length of the support column 11 to be engaged with the diaper 200 is long on the crotch portion C side and short on the distal end portion side of each of the front side region F and the back side region B. Therefore, the positions of the protruding portions 12 of the hook portions 9 aligned in the front-back direction LD are directed from the crotch portion C side to the distal end portion side of each of the front side region F and the back side region B, do not overlap each other on a longitudinal straight line in the front-back direction LD, and are aligned obliquely with respect to the front-back direction LD. As a result, similarly to the fourth example, it is possible to obtain the absorbent article 100 which has a strong engaging force upward in the front-back direction LD, is hardly displaced, and easily slides downward in the front-back direction LD. That is, in a case where an upward force in the front-back direction LD is applied to the absorbent article 100 when the diaper 200 to which the absorbent article 100 is attached is taken off, a nonwoven fabric fiber entangled with the hook portion 9 moves in a root direction of the protruding portion 12, and depending on an attachment angle of the hook member 8, the nonwoven fabric fiber moves in the direction of the base portion 10 through the support column 11 oblique to the diaper 200 to maintain the engagement between the nonwoven fabric fiber and the hook portion 9. Therefore, the absorbent article 100 is less likely to be peeled off or displaced from the diaper 200.

Meanwhile, in a case where a downward force in the front-back direction LD is applied to the absorbent article 100 when the diaper 200 to which the absorbent article 100 is attached is put on, a nonwoven fabric fiber entangled with the hook portion 9 is released from the protruding portion 12 of the hook portion 9, and since the hook member 8 is attached obliquely to the diaper 200, the protruding portion 12 from which the nonwoven fabric fiber has been released and a protruding portion 12 adjacent thereto are not aligned on a longitudinal straight line in the front-back direction LD and are aligned obliquely with respect to the front-back direction LD. Therefore, the nonwoven fabric fiber that has been released from the hook portion 9 is not engaged with the adjacent protruding portion 12, the absorbent article 100 slides downward in the front-back direction LD with movement of the body, and the absorbent article 100 is more likely to be brought into close contact with the diaper 200.

The hook member 8 having the support columns 11 of the same length can be more easily manufactured or prepared than the hook member 8 formed of the hook portions 9 having the support columns 11 of different lengths as in the fourth example of FIG. 12. As illustrated in FIG. 13(b), when the hook member 8 having a large number of hook portions 9 in which the lengths 11L of the support columns 11 are the same is attached to the recess 14, an effect that the hook member 8 is obliquely engaged with the diaper 200 can be obtained. Therefore, the hook member 8 in which a large number of hook portions 9 having the same shape are gathered or the hook member 8 having a large number of hook portions 9 in which the lengths 11L of the support columns 11 are the same and the shapes of the protruding portions 12 are different may be used. The shapes of the protruding portions 12 may be different from or the same as each other, and are not limited.

The hook member 8 formed of the hook portions 9 having the support columns 11 of different lengths illustrated in FIG. 12 may be attached to the recess 14. In this case, the protruding portion 12 of the hook portion 9 is engaged with the diaper 200 obliquely in the front-back direction LD at a steeper angle than a case where the hook member 8 having the support columns 11 of the same length is attached, and the effect may be further obtained.

As illustrated in FIG. 14(a), a shape may be adopted in which a part of the hook member 8 intersects with an auxiliary line and a part of the hook member 8 protrudes from the recess 14. However, since a portion obliquely engaged with the diaper 200 exhibits the effect, a portion protruding from the recess 14 is preferably small. In addition, if a hook member 8 which is small relative to the recess 14 is attached to a deep portion near an end point of the recess 14, and the support column 11 does not reach the auxiliary line 16, the absorbent article 100 and the diaper 200 are not engaged with each other, which is not preferable. Not all the support columns 11 of the hook member 8 need to intersect with the auxiliary line 16. However, at least 50% of the support columns 11 of the hook portions 9 in the hook member 8 preferably intersects with the auxiliary line 16, and 75% or more of the support columns 11 more preferably straddle the auxiliary line 16. The shapes of the hook portions 9 may be different from or the same as each other, and are not limited.

In the fifth example, as illustrated in FIGS. 13 and 14, the convex 15 high in the thickness direction of the absorbent article 100 is formed at an end point of the recess 14. However, the absorbent article 100 can be attached to the diaper 200 even if the absorbent article 100 does not have the convex 15 as illustrated in FIG. 15. However, in a case where there is no convex 15, as illustrated in FIG. 15, in the absorbent article 100, the thickness of the absorbent article 100 monotonously decreases from the recess 14 toward a distal end portion, and the absorbent article 100 is attached along the diaper 200. Therefore, the support column 11 is more likely to be attached vertically to the diaper 200, and there is a high possibility that the effect exhibited when the support column 11 is obliquely attached to the diaper 200 cannot be obtained. The convex 15 of the absorbent article 100 reduces a possibility that the diaper 200 is attached in parallel with the hook member 8 along the recess 14, and makes it easy to attach the diaper 200 obliquely to the support column 11. Therefore, the convex 15 high in the thickness direction is preferably formed at an end point of the recess 14 of the absorbent article 100.

INDUSTRIAL APPLICABILITY

The present invention can be used for all absorbent articles such as a pad type or flat type absorbent article as in the above examples.

REFERENCE SIGNS LIST

4 Top sheet
5 Back sheet
6 Absorber
7 Gather elastic member
8 Hook member (of mechanical fastener)
9 Hook portion
10 Base portion
11 Support column
12 Protruding portion
13 Gap
14 Recess
15 Convex
16 Auxiliary line
17 Folding line
100 Absorbent article
200 Outer such as diaper
WD Width direction
LD Front-back direction
BS Three-dimensional gather
C Crotch portion
F Front side region
B Back side region

The invention claimed is:
1. An absorbent article having a crotch portion, a front side region on a front side of the crotch portion, and a back side region on a back side of the crotch portion,
comprising: a front surface sheet configured to face a skin of a wearer; a back surface sheet located on a side opposite to the front surface sheet; and an attachment member which is formed in each of the front side region and the back side region of the back surface sheet, and by means of which the absorbent article can be removably attached to an inner surface of an outer article, wherein the attachment member is a hook member of a mechanical fastener, the hook member is formed of a sheet-like base portion and a plurality of hook portions, the hook portion has a support column extending from the base portion and a protruding portion at an end of the support column on the base portion, in each of the large number of hook portions located in the front side region, the protruding portion extends in a front-back direction, and a length of a front side of the protruding portion is longer than a length of a back side of the protruding portion, or the protruding portion extends to a front side in the front-back direction, and in each of the large number of hook portions located in the back side region, the protruding portion extends in the front-back direction, and a length of a back side of the protruding portion is longer than a length of a front side of the protruding portion, or the protruding portion extends to a back side in the front-back direction.

2. The absorbent article according to claim 1,
wherein the support column of the hook portion becomes thinner as it goes from the base portion toward the protruding portion.

3. The absorbent article according to claim 1,
wherein the support column of the hook portion extends from the base portion as a start point, the support column extends from a crotch portion side to a front side in the hook portion located in the front side region, and the support column extends from the crotch portion side to a back side in the hook portion located in the back side region.

4. The absorbent article according to claim 1,
wherein in the mechanical fastener attached to the front side region, a length of the support column of the hook portion located on a front side is getting shorter, and a length of the support column of the hook portion located on a crotch portion side is getting longer, and in the mechanical fastener located in the back side region, a length of the support column of the hook portion located on a back side is getting shorter, and a length of the support column of the hook portion located on the crotch portion side is getting longer.

5. The absorbent article according to claim 1,
wherein a recess is formed in the front-back direction in each of the front side region and the back side region of the back surface sheet, the recess in the front side region is formed so as to be deeper on a front side than on a crotch portion side, a convex high in a thickness direction is formed at a front side end of the recess, the recess in the back side region is formed so as to be deeper on a back side than on the crotch portion side, a convex high in the thickness direction is formed at a back side end of the recess, the hook member in which lengths of the support columns of the hook portions are equal to each other is fixed to the recess, and the support columns of the hook member are present on a line connecting a start point of the recess located on the crotch portion side and a vertex of the convex in the front-back direction.

* * * * *